(12) United States Patent
Xiong et al.

(10) Patent No.: US 12,188,907 B2
(45) Date of Patent: Jan. 7, 2025

(54) ULTRASONIC GAS SENSOR

(71) Applicant: CUBIC SENSOR AND INSTRUMENT CO., LTD, Wuhan (CN)

(72) Inventors: Youhui Xiong, Wuhan (CN); Jun Wu, Wuhan (CN); Chongyang Li, Wuhan (CN); Chunlong Fan, Wuhan (CN); Li Zhu, Wuhan (CN)

(73) Assignee: CUBIC SENSOR AND INSTRUMENT CO., LTD, Wuhan (CN)

( * ) Notice: Subject to any disclaimer, the term of this patent is extended or adjusted under 35 U.S.C. 154(b) by 298 days.

(21) Appl. No.: 17/832,728

(22) Filed: Jun. 6, 2022

(65) Prior Publication Data

US 2022/0299480 A1    Sep. 22, 2022

Related U.S. Application Data

(63) Continuation of application No. PCT/CN2020/139645, filed on Dec. 25, 2020.

(30) Foreign Application Priority Data

Dec. 26, 2019 (CN) .......................... 201911370604.4

(51) Int. Cl.
  *G01N 29/22*  (2006.01)
  *G01N 29/02*  (2006.01)
(52) U.S. Cl.
  CPC ........... *G01N 29/222* (2013.01); *G01N 29/02* (2013.01); *G01N 29/221* (2013.01); *G01N 2291/0215* (2013.01)

(58) Field of Classification Search
  CPC .... G01N 29/222; G01N 29/02; G01N 29/221; G01N 2291/0215; G01N 2291/021;
  (Continued)

(56) References Cited

U.S. PATENT DOCUMENTS 5,351,522 A    10/1994  Lura
5,625,156 A *  4/1997  Serrels ................. F01N 13/008
                                                    73/863.81
(Continued)

FOREIGN PATENT DOCUMENTS

CN    201803811 U    4/2011
CN    201828541 U    5/2011
(Continued)

*Primary Examiner* — Robert R Raevis
(74) *Attorney, Agent, or Firm* — True Shepherd LLC; Andrew C. Cheng

(57) ABSTRACT

An ultrasonic gas sensor includes a housing, and a first ultrasonic transducer and a second ultrasonic transducer that are separately arranged at a top of an inner chamber of the housing, where the first ultrasonic transducer and the second ultrasonic transducer form a V-shaped ultrasonic transmission path in the housing; the housing is provided therein with a gas inlet channel and a gas outlet channel; an upper end of the gas inlet channel is close to the first ultrasonic transducer, and an upper end of the gas outlet channel is close to the second ultrasonic transducer, such that a measured gas flow entering a bypass tube passes through a detection area of the first ultrasonic transducer and the second ultrasonic transducer; a lower end of the gas inlet channel and a lower end of the gas outlet channel communicate with a gas sensor mount.

13 Claims, 6 Drawing Sheets

A-A

(58) Field of Classification Search
CPC ....... G01N 2291/02809; G01N 29/024; A61M 16/0816; A61M 2016/003; A61M 2205/3334; A61M 2205/3375
USPC .... 73/23.28, 24.01–24.6, 32 A, 592, 863.41, 73/863.51, 863.81, 864.73, 861.27–861.31
See application file for complete search history.

(56) References Cited

U.S. PATENT DOCUMENTS

| | | | |
|---|---|---|---|
| 5,844,148 A | * | 12/1998 | Klein ................... G01N 1/2226 |
| | | | 73/864.81 |
| 10,254,390 B2 | | 4/2019 | Bartsch et al. |
| 11,231,393 B2 | | 1/2022 | Massey et al. |

FOREIGN PATENT DOCUMENTS

| | | | | |
|---|---|---|---|---|
| CN | 102441213 B | | 5/2012 | |
| CN | 103201599 B | | 7/2013 | |
| CN | 103630271 A | | 3/2014 | |
| CN | 204536268 U | | 8/2015 | |
| CN | 106248148 B | | 12/2016 | |
| CN | 206362763 U | | 7/2017 | |
| CN | 208536932 U | | 2/2019 | |
| CN | 210135957 U | * | 3/2020 | |
| CN | 110988115 A | | 4/2020 | |
| CN | 210952976 U | * | 7/2020 | |
| CN | 211697651 U | | 10/2020 | |
| JP | 2006308401 A | | 11/2006 | |
| KR | 20200113377 A | * | 10/2020 | |
| WO | WO-2018002612 A1 | * | 1/2018 | ............... G01H 5/00 |

\* cited by examiner

ULTRASONIC GAS SENSOR

CROSS-REFERENCE TO RELATED APPLICATIONS

This application is a continuation of International Patent Application No. PCT/CN2020/139645 with a filing date of Dec. 25, 2020, designating the United States, now pending, and further claims priority to Chinese Patent Application No. 201911370604.4 with a filing date of Dec. 26, 2019. The content of the aforementioned applications, including any intervening amendments thereto, are incorporated herein by reference.

TECHNICAL FIELD

The present disclosure relates to the technical field of gas sensors and more particularly to an ultrasonic gas sensor.

BACKGROUND ART

Medical devices, such as ventilators and anesthesia machines, need to monitor the concentration of oxygen, anesthetic gas, hydrogen and other gases in the delivered mixed gas through gas sensors. The gas sensor transmits the acquired gas concentration data to the control unit of the ventilator and anesthesia machine. The control unit processes the detection data, and adjusts the flow rate of the gas branch according to the detection results.

Traditional gas sensors are based on electrochemical principles to detect the aforementioned gases. For example, patent document CN102441213B provides an anesthesia machine with an electrochemical oxygen sensor. It realizes the measurement of oxygen concentration according to the mechanism that oxygen molecules react with specific chemical substances inside the oxygen sensor to generate electric current. The oxygen concentration is linearly related to the magnitude of the generated current, so the oxygen concentration can be measured according to the magnitude of the generated current. However, with the increase of use time, the morphology of the chemical substances inside the oxygen sensor will change, and the corresponding relationship between the oxygen concentration and the current will change. Therefore, the oxygen sensor needs to be calibrated or even replaced. The existing electrochemical oxygen sensor is provided in the mount of the ventilator or anesthesia machine, and the calibration requires complicated and time-consuming manual intervention, resulting in high cost and short lifespan of the gas sensor.

In order to achieve long lifespan and low cost of the gas sensor, in the prior art, the gas flow entering the sensor is detected by ultrasonic detection technology so as to obtain the concentration of the gas to be measured in the gas flow. Patent document CN106248148B proposes a technical solution for detecting the gas flow entering the sensor by ultrasonic detection technology so as to obtain the oxygen concentration in the gas flow, and provides a through-beam ultrasonic gas sensor. Patent document CN103201599B provides a V-shaped ultrasonic flow sensor. In these two gas measurement devices, the gas inlet and the gas outlet are located at two ends of the gas chamber respectively, and need to be connected to the measuring tube section through connecting tubes. In the existing mainstream ventilators and anesthesia machines, the measuring tube section usually only has a fixed mounting hole for mounting the oxygen sensor, and there is no additional connecting tube. Therefore, no gas flow channel can be directly formed between the existing ultrasonic sensor and the oxygen sensor mount for matched mounting.

SUMMARY

In view of this, an embodiment of the present disclosure provides an ultrasonic gas sensor. The present disclosure replaces the existing electrochemical gas sensor to achieve a long lifespan and avoid manual intervention. The present disclosure matches the gas sensor mounting hole of the existing mainstream ventilator, anesthesia machine, etc., and overcomes the defect that the existing traditional through-beam and V-shaped ultrasonic gas sensors need an additional measuring tube section for matched mounting.

The ultrasonic gas sensor provided by the embodiment of the present disclosure includes a housing, and a first ultrasonic transducer and a second ultrasonic transducer arranged at a top of an inner chamber of the housing, where the first ultrasonic transducer and the second ultrasonic transducer form a V-shaped ultrasonic transmission path in the housing; the housing is sealed by a bottom plate at a bottom of the inner chamber of the housing; the bottom of the housing is provided therein with a gas inlet channel and a gas outlet channel; an upper end of the gas inlet channel extends into a left side of the ultrasonic transmission path, and an upper end of the gas outlet channel extends into a right side of the ultrasonic transmission path; a lower end of the gas inlet channel and a lower end of the gas outlet channel are converged at a lower side of the bottom plate of the housing, and are separated by a baffle plate protruding from the lower side of the bottom plate of the housing; and the lower end of the gas inlet channel and the lower end of the gas outlet channel communicate with a gas sensor mount.

The upper end of the gas inlet channel may be close to the first ultrasonic transducer, and the upper end of the gas outlet channel may be close to the second ultrasonic transducer, such that a measured gas flow entering the inner chamber of the housing passes through a detection area of the first ultrasonic transducer and the second ultrasonic transducer.

The inner chamber of the housing may be a V-shaped structure with left-right symmetry; the housing may be sealed, and communicates with the gas sensor mount through the gas inlet channel and the gas outlet channel; and the gas inlet channel and the gas outlet channel may be circular.

The baffle plate may extend downwardly into the gas sensor mount, and may have a lower end not in contact with a bottom of the gas sensor mount, so as to form a splitting gap.

The baffle plate may extend downwardly into the gas sensor mount, and may have a lower end in contact with a bottom of the gas sensor mount.

A downwardly extending connecting portion may be provided at a lower end of the housing, through which the housing may be connected to the gas sensor mount; and the connecting portion may be hollow inside and communicates with the gas inlet channel and the gas outlet channel.

A downward extension length L1 of the baffle plate may be greater than or equal to a downward extension length L2 of the connecting portion.

The lower end of the housing may be connected to the gas sensor mount by screwing or snapping.

An upper end of the housing may be provided with a first mounting groove and a second mounting groove, which may be respectively configured to mount the first ultrasonic transducer and the second ultrasonic transducer.

A diameter-reducing structure close to the upper end of the gas inlet channel may be provided on the ultrasonic transmission path.

The diameter-reducing structure may be an arc-shaped transition section.

The baffle plate may be provided with an inclined baffling surface on a side close to the lower end of the gas inlet channel.

The baffle plate may be provided with an inverted V- or Y-shaped cross-section.

The technical solution provided by the embodiment of the present disclosure has the following beneficial effects:

The present disclosure abandons the traditional gas chamber with a square cross-section, and adopts the gas chamber with a V-shaped cross-section, such that the ultrasonic signal emission path is consistent with the internal shape of the gas chamber, so as to reduce the sensor volume. In the present disclosure, the gas inlet channel and the gas outlet channel have their upper ends separated from each other and lower ends converged, which is matched with the traditional gas sensor mount.

The present disclosure eliminates the need for an additional connecting tube and utilizes the latest ultrasonic technology to replace the traditional electrochemical gas sensor. It has the advantages of long lifespan, low cost, no need for manual calibration, compact structure, easy mounting and fast response speed.

In the present disclosure, the ultrasonic transmission path is reduced in diameter, and the baffle plate is provided with a baffling surface, which accelerates the gas flow, improves the gas concentration measurement response speed, and improves the detection accuracy.

Figure 1:
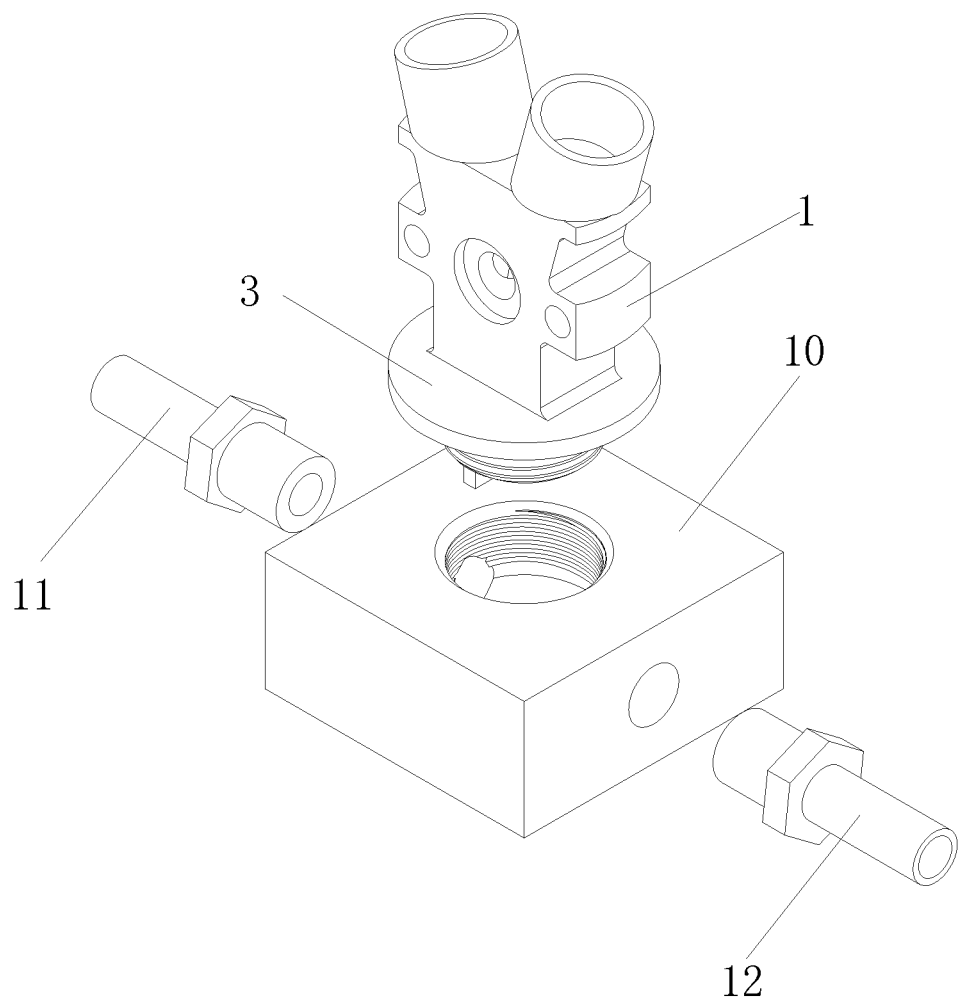
FIG. 1 is an exploded view of an ultrasonic gas sensor and a gas sensor mount which are fitted with each other according to the present disclosure.

REFERENCE NUMERALS 1. housing; 2. ultrasonic transmission path; 2a. arc-shaped transition section; 3. bottom plate; 4. first mounting groove; 5. second mounting groove; 6. gas inlet channel; 6a. upper end of gas inlet channel; 6b. lower end of gas inlet channel; 7. gas outlet channel; 7a. upper end of gas outlet channel; 7b. lower end of gas outlet channel; 8. connecting portion; 9. baffle plate; 9a. baffling surface; 10. gas sensor mount; 11. gas inlet connector; and 12. gas outlet connector.

DETAILED DESCRIPTION OF THE EMBODIMENTS

In order to make the objectives, technical solutions and advantages of the present disclosure clearer, the implementations of the present disclosure will be further described in detail in conjunction with the drawings.

Embodiment 1

Referring to FIG. 1, an embodiment of the present disclosure provides an ultrasonic gas sensor for measuring a concentration of oxygen, anesthetic gas, hydrogen and other gases. In this embodiment, the measurement of oxygen is only used as an example, and the present disclosure is not limited thereto. The ultrasonic gas sensor includes a housing 1 and a pair of ultrasonic transducers, namely a first ultrasonic transducer and a second ultrasonic transducer.

Figure 2:
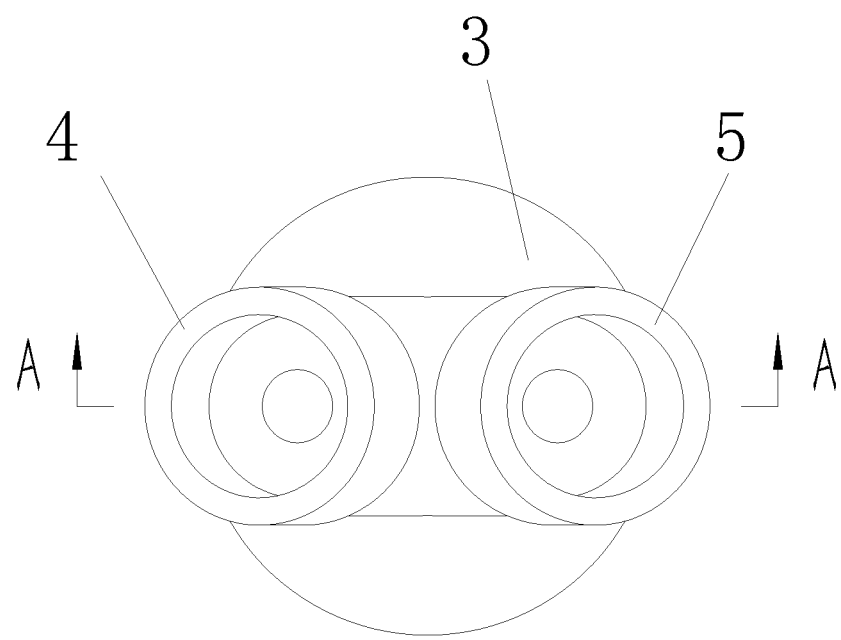
FIG. 2 is a top view of a housing 1 shown in FIG. 1.
Figure 3:
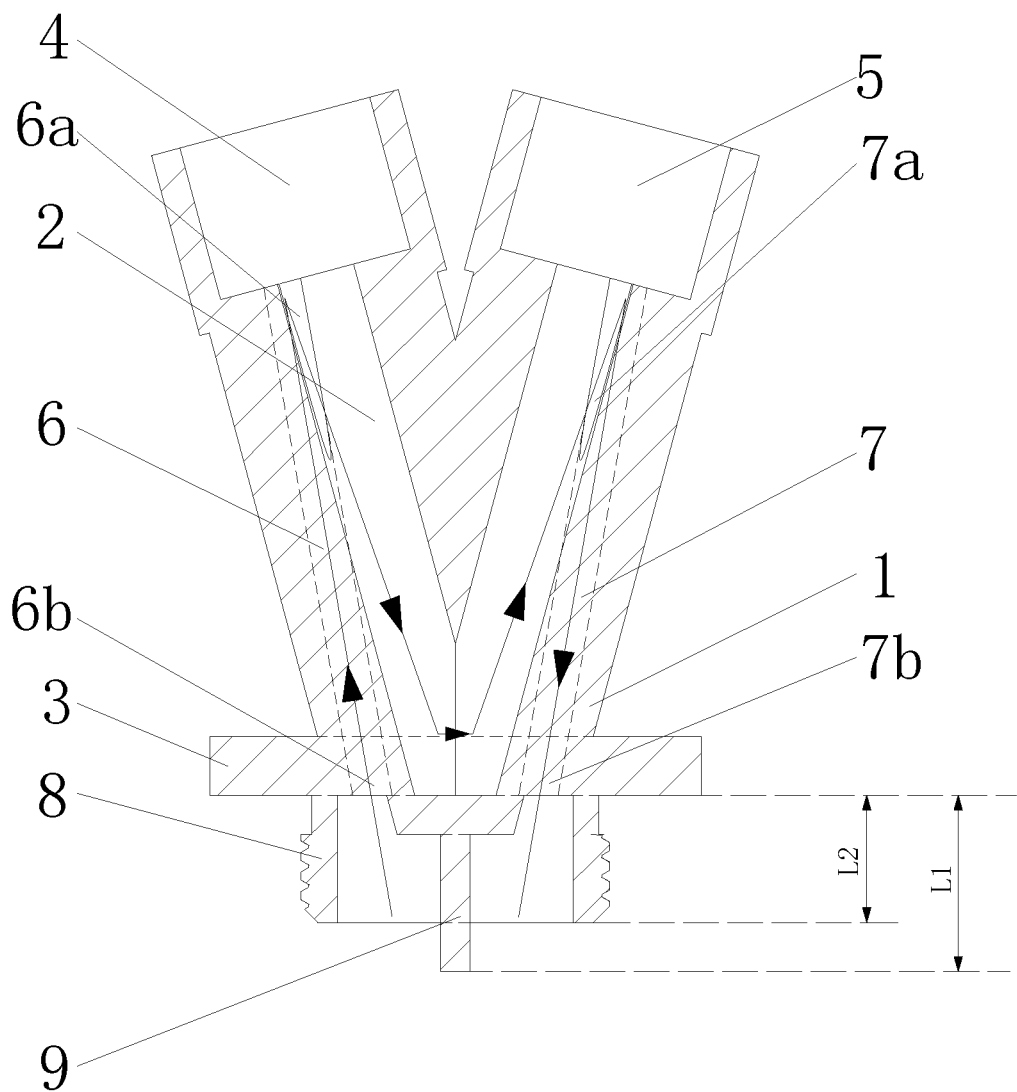
FIG. 3 is a sectional view taken along line A-A shown in FIG. 2.
Figure 4:
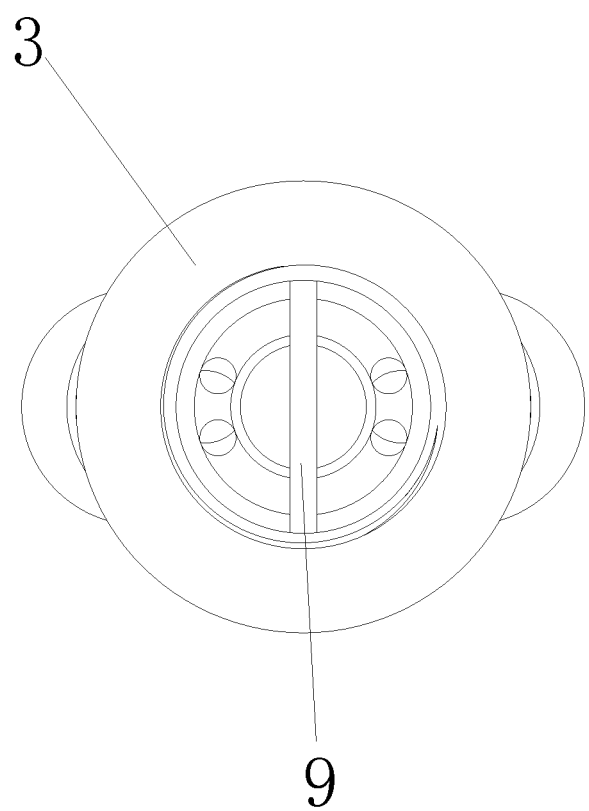
FIG. 4 is a bottom view of the housing 1 shown in FIG. 1.

Referring to FIGS. 2, 3 and 4, an inner chamber of the housing 1 is a V-shaped structure with left-right symmetry. The first ultrasonic transducer and the second ultrasonic transducer are located at a top of the housing 1, and a V-shaped ultrasonic transmission path 2 is formed between the first ultrasonic transducer and the second ultrasonic transducer. Specifically, the first ultrasonic transducer is provided in a first mounting groove 4, and the second ultrasonic transducer is provided in a second mounting groove 5. The first ultrasonic transducer transmits an ultrasonic signal along the V-shaped ultrasonic transmission path 2, and the ultrasonic signal is reflected by a bottom plate 3 at a bottom of the inner chamber of the housing 1. The reflected ultrasonic signal continues to propagate to the second ultrasonic transducer along the V-shaped ultrasonic transmission path 2, and is received by the second ultrasonic transducer.

Referring to FIGS. 2 and 3, the housing 1 is further provided with a gas inlet channel 6 and a gas outlet channel 7. The gas inlet channel 6 and the gas outlet channel 7 are provided with cylindrical holes. An upper end 6a of the gas inlet channel 6 is close to the first ultrasonic transducer, and an upper end 7a of the gas outlet channel 7 is close to the second ultrasonic transducer. Therefore, a measured gas flow entering the inner chamber of the housing 1 can pass through the detection areas of the first ultrasonic transducer and the second ultrasonic transducer, thereby reducing the "dead zone" of ultrasonic detection. A lower end 6b of the gas inlet channel 6 and a lower end 7b of the gas outlet channel 7 are converged at a lower side of the bottom plate 3 at the bottom of the housing 1, and are separated through a baffle plate 9 protruding from the lower side of the bottom plate 3 of the housing 1. The lower end 6b of the gas inlet channel 6 and the lower end 7b of the gas outlet channel 7 communicate with a gas sensor mount 10.

Figure 5:
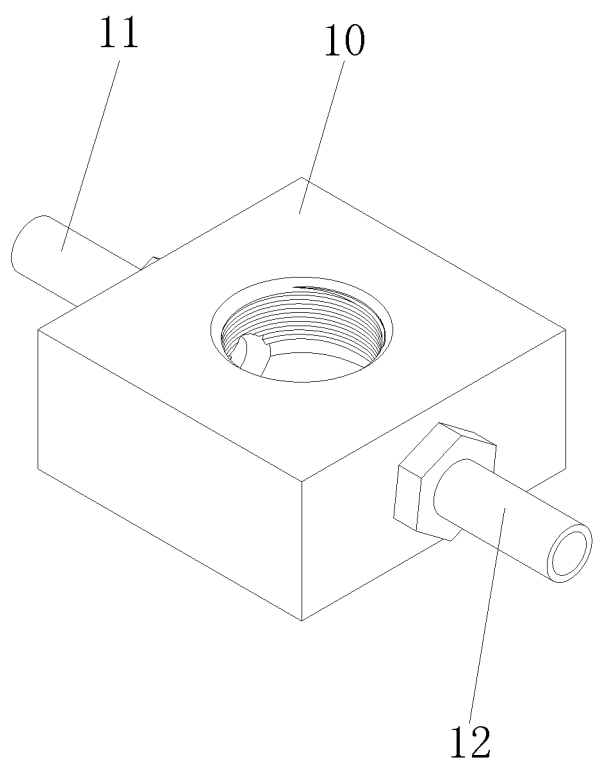
FIG. 5 is a schematic view of the gas sensor mount 10 shown in FIG. 1.

Referring to FIGS. 1 and 5, in order to improve the response speed of the sensor, a baffle plate 9 is provided between the lower end 6b of the gas inlet channel 6 and the lower end 7b of the gas outlet channel 7. The baffle plate 9 extends downwardly from the bottom plate 3 of the housing 1 into the gas sensor mount 10.

In this embodiment, two ends of the gas sensor mount 10 are provided with a gas inlet connector 11 and a gas outlet connector 12 that communicate with each other. The gas sensor mount 10 is a rectangular member, and the gas inlet connector 11 and the gas outlet connector 12 are tubular connectors, which are respectively provided on two opposite sides of the gas sensor mount 10. In fact, the present disclosure does not limit the structure of the gas sensor mount 10. Through the baffle plate 9, more gas to be measured entering from the gas inlet connector 11 can enter the V-shaped ultrasonic transmission path 2 through the gas inlet channel 6, and flow out of the V-shaped ultrasonic transmission path 2 through the gas outlet channel 7. This design accelerates the flow of the gas to be measured between the first ultrasonic transducer and the second ultrasonic transducer, and improves the response speed of the oxygen concentration measurement.

A downwardly extending connecting portion 8 is provided at a lower end of the housing 1. The housing 1 is connected to the gas sensor mount 10 through the connecting portion 8. The connecting portion 8 is hollow inside and communicates with the gas inlet channel 6 and the gas outlet channel 7. A downward extension length L1 of the baffle plate 9 is greater than or equal to a downward extension length L2 of the connecting portion.

If the oxygen flow rate of the measuring tube section is small, a lower end of the baffle plate 9 is in contact with a bottom of the gas sensor mount 10. In this way, all the gas flow entering from the gas inlet connector 11 is blocked by the baffle plate 9 and then enters the gas inlet channel 6 to ensure the flow speed of the gas flow entering the ultrasonic transmission path 2.

If the oxygen flow rate of the measuring tube section is large, the lower end of the baffle plate 9 is not in contact with the bottom of the gas sensor mount 1, so as to form a splitting gap. In this way, a part of the gas flow entering from the gas inlet connector 11 is blocked by the baffle plate 9 and then enters the gas inlet channel 6, and another part of the gas flow directly flows to the gas outlet connector 12 through the splitting gap. This design ensures the flow speed of the gas flow entering the ultrasonic transmission path 2, reduces the influence of oxygen detection on oxygen delivery of the ventilator or anesthesia machine, and eliminates the influence of unstable gas flow on the measurement accuracy of oxygen concentration.

In order to accurately measure the gas temperature in real time, a temperature sensor is provided in a middle of a gas flow path of the ultrasonic gas sensor.

The ultrasonic gas sensor of the present disclosure is used in conjunction with an external printed circuit board assembly (PCBA). The PCBA is connected to the first ultrasonic transducer, the second ultrasonic transducer and the temperature sensor to realize real-time measurement of gas concentration.

In this embodiment, the application of the ultrasonic gas sensor to the gas sensor mount of the medical device such as the ventilator or the oxygen generator is taken as an example for description. In fact, it can also be applied to other occasions where a gas sensor mount similar to that used in this embodiment is used to form a detection channel, which is not limited herein.

Embodiment 2

Figure 6:
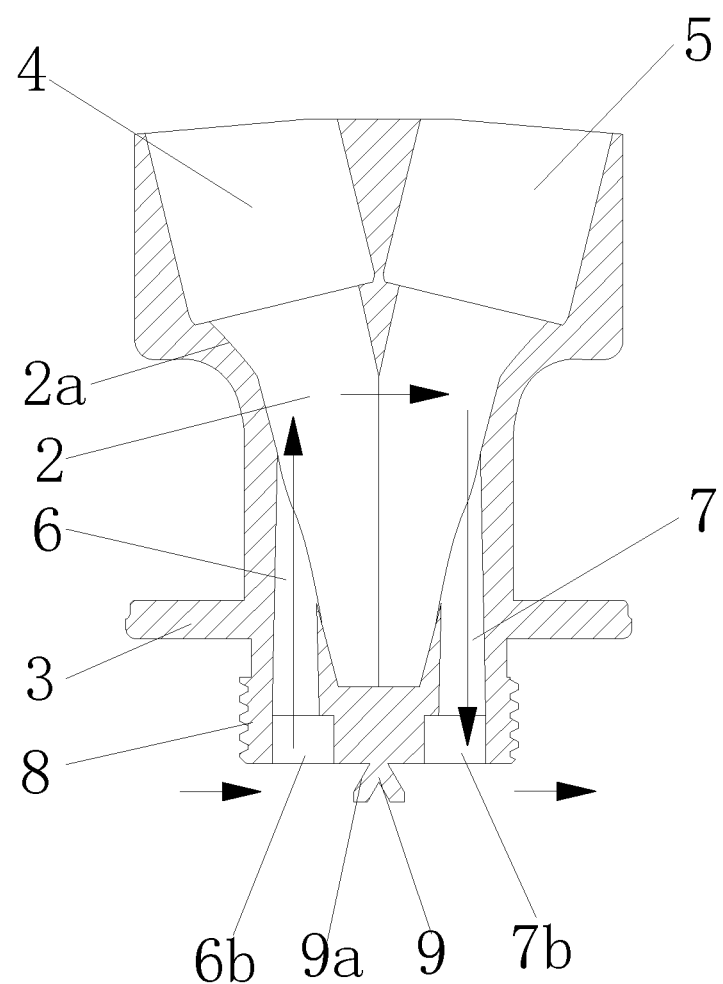
FIG. 6 is a sectional view of an ultrasonic gas sensor according to another embodiment of the present disclosure.

Referring to FIG. 6, the ultrasonic gas sensor of Embodiment 2 differs that of Embodiment 1 in the structures of the V-shaped ultrasonic transmission path 2 and the baffle plate 9.

Specifically, a diameter-reducing structure close to the upper end of the gas inlet channel 6 is provided on the ultrasonic transmission path 2. In this embodiment, an arc-shaped transition section 2a close to the upper end of the gas inlet channel 6 is provided on the ultrasonic transmission path 2. The arc-shaped transition section 2a has a smaller diameter when it is closer to the upper end of the gas inlet channel 6. Since the cross-sectional area of the gas flow channel close to the upper end of the gas inlet channel 6 is reduced, the gas flow is accelerated, and the response speed of the gas concentration measurement is improved.

In order to increase the entry speed of the lower end 6b of the gas inlet channel, the baffle plate 9 is provided with an inclined baffling surface 9a on a side close to the lower end 6b of the gas inlet channel. The baffling surface 9a promotes more gas to be measured to enter the gas flow at the lower end 6b of the gas inlet channel, and promotes more gas flow to directly enter the lower end 6b of the gas inlet channel. This design prevents the measured gas flow from bypassing the baffle plate 9 and directly reaching a gas outlet 7b without entering the lower end 6b of the gas inlet channel. It further accelerates the gas flow and improves the response speed of the gas concentration measurement. Preferably, the baffle plate 9 is provided with an inverted V- or Y-shaped cross-section.

In the specification, the orientation terms such as "front", "rear" "upper", and "lower" are defined based on the positions of the parts in the drawings, which are merely intended for clarity and convenience of expressing the technical solution. It should be understood that the use of such orientation terms should not limit the protection scope claimed by the present disclosure.

The above embodiments and the features of the embodiments herein may be combined with each other without conflict.

The above described are merely preferred embodiments of the present disclosure, and are not intended to limit the present disclosure. Any modifications, equivalent replacements and improvements made within the spirit and principle of the present disclosure should be all included in the protection scope of the present disclosure.

What is claimed is:

1. An ultrasonic gas sensor, comprising a housing, a gas sensor mount for supporting the housing, and a first ultrasonic transducer and a second ultrasonic transducer separately housed in the housing, wherein a V-shaped ultrasonic transmission path is formed between the first ultrasonic transducer and the second ultrasonic transducer in the housing; a gas inlet channel and a gas outlet channel are defined in the housing; an upper end of the gas inlet channel extends into a left side of the V-shaped ultrasonic transmission path, and an upper end of the gas outlet channel extends into a right side of the V-shaped ultrasonic transmission path; a lower end of the gas inlet channel and a lower end of the gas outlet channel are converged towards each other and extended to a lower side of a bottom plate of the housing, and the lower end of the gas inlet channel and the lower end of the gas outlet channel are separated by a baffle plate protruding from the lower side of the bottom plate of the housing; and the lower end of the gas inlet channel and the lower end of the gas outlet channel are in gas communication with a chamber formed in the gas sensor mount.

2. The ultrasonic gas sensor according to claim 1, wherein the upper end of the gas inlet channel is close to the first ultrasonic transducer, and the upper end of the gas outlet channel is close to the second ultrasonic transducer, such that a measured gas flow entering the V-shaped ultrasonic transmission path passes through a detection area of the first ultrasonic transducer and the second ultrasonic transducer.

3. The ultrasonic gas sensor according to claim 1, wherein the V-shaped ultrasonic transmission path is a V-shaped structure with left-right symmetry; and the gas inlet channel and the gas outlet channel are circular.

4. The ultrasonic gas sensor according to claim 3, wherein the baffle plate extends downwardly into the gas sensor mount, and has a lower end not in contact with a bottom of the gas sensor mount, so as to form a splitting gap.

5. The ultrasonic gas sensor according to claim 3, wherein the baffle plate extends downwardly into the gas sensor mount, and has a lower end in contact with a bottom of the gas sensor mount.

6. The ultrasonic gas sensor according to claim 3, wherein a downwardly extending connecting portion is provided at a lower end of the bottom plate, through which the housing is connected to the gas sensor mount.

7. The ultrasonic gas sensor according to claim 6, wherein a downward extension length L1 of the baffle plate is greater than or equal to a downward extension length L2 of the connecting portion.

8. The ultrasonic gas sensor according to claim 6, wherein the downwardly extending connecting portion is connected to the gas sensor mount by screwing or snapping.

9. The ultrasonic gas sensor according to claim 1, wherein an upper end of the housing is provided with a first mounting groove and a second mounting groove, which are respectively configured to mount the first ultrasonic transducer and the second ultrasonic transducer.

10. The ultrasonic gas sensor according to claim 1, wherein a diameter-reducing structure close to the upper end of the gas inlet channel is provided on the V-shaped ultrasonic transmission path.

11. The ultrasonic gas sensor according to claim 10, wherein the diameter-reducing structure is an arc-shaped transition section.

12. The ultrasonic gas sensor according to claim 1, wherein the baffle plate is provided with an inclined baffling surface on a side close to the lower end of the gas inlet channel.

13. The ultrasonic gas sensor according to claim 12, wherein the baffle plate is provided with an inverted V- or Y-shaped cross-section.

* * * * *